United States Patent [19]

Spicer et al.

[11] Patent Number: 4,499,190

[45] Date of Patent: Feb. 12, 1985

[54] METHOD OF DETECTING SULFUR DIOXIDE

[75] Inventors: Leonard D. Spicer, Salt Lake City, Utah; Dennis W. Bennett, Clemson, S.C.; Jon F. Davis, Salt Lake City, Utah

[73] Assignee: The United States of America as represented by the United States Department of Energy, Washington, D.C.

[21] Appl. No.: 490,551

[22] Filed: May 9, 1983

Related U.S. Application Data

[63] Continuation of Ser. No. 273,174, Jun. 12, 1981, abandoned.

[51] Int. Cl.³ .................... C07F 7/10; G01N 21/64; G01N 21/77; G01N 24/08
[52] U.S. Cl. .................... 436/122; 324/308; 324/315; 436/172; 436/173; 556/410; 556/428
[58] Field of Search .................... 436/122, 172, 173; 556/410, 428

[56] References Cited

U.S. PATENT DOCUMENTS 3,973,911  8/1976  Von Smolinski et al. ... 23/232 R X
4,459,421  7/1984  Spicer et al. .................... 556/410

OTHER PUBLICATIONS

Davis et al., Chemical Abstracts, vol. 93, 1980, p. 989, No. 93, 71846m.
Bennett et al., Chemical Abstracts, vol. 95, 1981, p. 681, No. 95, 150743v.
Dyer, "Applications of Absorption Spectroscopy of Organic Compounds", Prentice-Hall, Inc., 1965, pp. 58-66.
Griffins, R. G., Anal. Chem., 1977, 49,951a.
Davis et al., Inorg. Chem., 1980, 19, 2191-2192.
Bennett et al., J. Am. Chem. Soc. 1981, 103, 5522-5526.
Debrun et al., Chem. Abstracts, vol. 78, 1973, p. 267, No. 151907n.

Primary Examiner—Arnold Turk
Attorney, Agent, or Firm—James W. Weinberger; Walter L. Rees

[57] ABSTRACT $(CH_3)_3SiNSO$ is produced by the reaction of $((CH_3)_3Si)_2NH$ with $SO_2$. Also produced in the reaction are $((CH_3)_3Si)_2O$ and a new solid compound $[NH_4][(CH_3)_3SiOSO_2]$. Both $(CH_3)_3SiNSO$ and $[NH_4][(CH_3)_3SiOSO_2]$ have fluorescent properties. The reaction of the subject invention is used in a method of measuring the concentration of $SO_2$ pollutants in gases. By the method, a sample of gas is bubbled through a solution of $((CH_3)_3Si)_2NH$, whereby any $SO_2$ present in the gas will react to produce the two fluorescent products. The measured fluorescence of these products can then be used to calculate the concentration of $SO_2$ in the original gas sample. The solid product $[NH_4][(CH_3)_3Si-OSO_2]$ may be used as a standard in solid state NMR spectroscopy.

12 Claims, 2 Drawing Figures

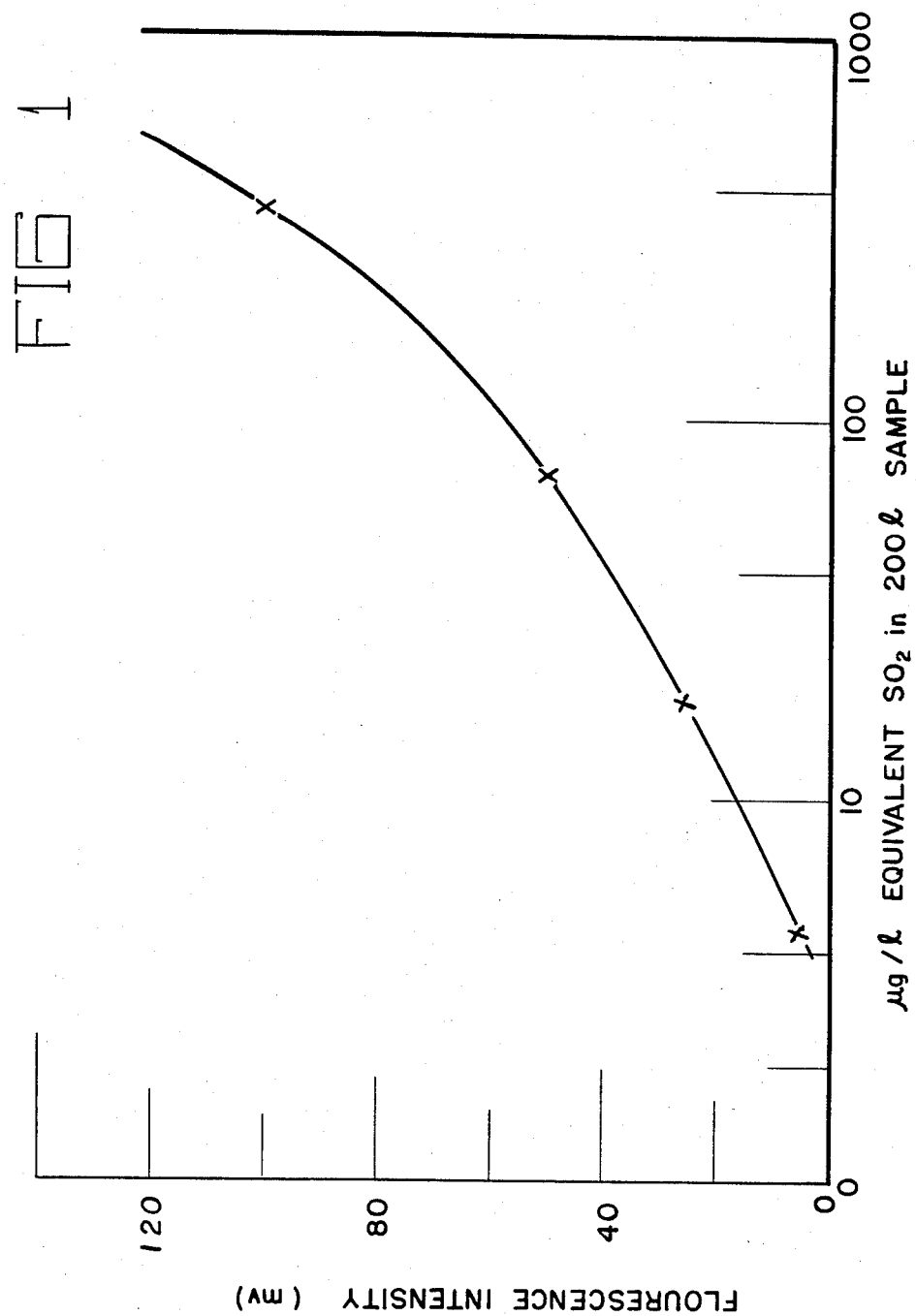

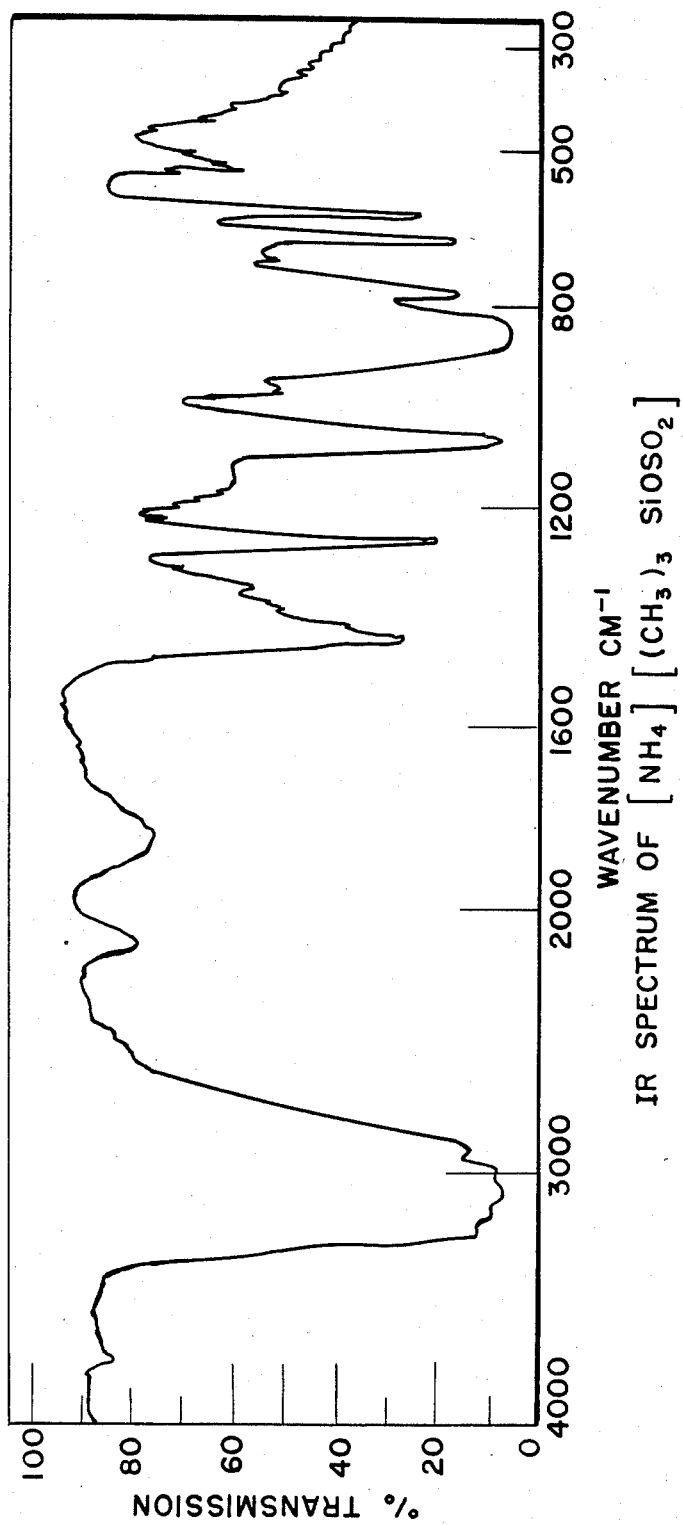

METHOD OF DETECTING SULFUR DIOXIDE

CONTRACTUAL ORIGIN OF THE INVENTION

The United States Government has rights in this invention pursuant to Contract No. EY-76-S-02-2190 between the U.S. Department of Energy and the University of Utah.

This is a continuation of application Ser. No. 273,174 filed June 12, 1981, now abandoned.

BACKGROUND OF THE INVENTION

This invention relates to a new chemical synthesis of 1,1,1-trimethyl-N-sulfinyl silanamine, $(CH_3)_3SiNSO$. It also relates to other uses of the same reaction and its byproducts.

$(CH_3)_3SiNSO$ is of great interest in the organosilicon industry. It is used in the synthesis of selected heterocycles, symmetric disulfides, and other sulfinylamines. It would be desirable to manufacture this compound by a simple and direct method with a rapid reaction rate and high yields. The compound was first synthesized by the reaction of tris(trimethylsilyl)amine with thionyl chloride at 70° C. in the presence of aluminum chloride catalyst. Other synthetic routes have since been reported in the chemical literature, such as the reaction of $(C_6H_5)SNSO$ with $(CH_3)_3SiS(C_6H_5)$ to produce the product of interest plus $(C_6H_5)_2S_2$, and the reaction of $(n-C_4H_9)_3SnNSO$ with covalent chlorides such as $(CH_3)_3SiCl$, to produce $(CH_3)_3SiNSO$ and $(n-C_4H_9)_3SnCl$. These synthetic routes are ill-suited to large-scale industrial production of the compound because they require exotic and expensive starting reagents and give unsatisfactory yields.

A method has been developed for the production of $(CH_3)_3SiNSO$ involving the direct reaction of $SO_2$ with a common silylating agent. The starting materials are relatively inexpensive, and the reaction proceeds to 100% completion at ambient temperatures.

In addition to providing a new and novel method for producing $(CH_3)_3SiNSO$, the same reaction may be used in a different way to measure the concentration of $SO_2$ in gases such as industrial stack gases or ambient air. $SO_2$ is a major air pollutant. Frequently, the quantity of $SO_2$ being released into the air must be monitored, particularly in an industrial setting. Several methods are currently being used for this purpose, including wet chemical and electroanalytical methods, $H_2$ flame photometry, and fluorescence. Wet chemical and electro-analytical techniques are often slow and their systems require frequent maintenance. $H_2$ flame photometry is unsatisfactory because the high flammability of $H_2$ is a major safety hazard and because other sulfur compounds may act as interferences. Techniques which measure the fluorescence of the $SO_2$ itself are subject to interference from other atmospheric oxides and hydrocarbons. It would be desirable to have a method for $SO_2$ analysis which would allow samples to be taken at remote sites far from the analytical laboratory. Ideally, the method would be reliable and simple to use. It would be highly specific, free of most interferences, accurate, and would require relatively inexpensive apparatus.

The reaction of the subject invention combines $SO_2$ and a common silylating agent to produce $(CH_3)_3SiNSO$ and $[NH_4][(CH_3)_3SiOSO_2]$. Both of these compounds have fluorescent properties. This reaction may be used to determine $SO_2$ conveniently and reliably in gases such as ambient air or industrial stack gases by passing a sample of the gas through the silylating agent to react any $SO_2$ in the gas with the silylating agent, exciting the reaction products to induce fluorescence, and measuring the fluorescence produced, the fluorescence of the the products being determinative of the quantity of $SO_2$ in the original gas sample.

In addition to these uses, the reaction of the subject invention also produces the new by-product $[NH_4][(CH_3)_3SiOSO_2]$. This compound has a new and unexpected use in the field of nuclear magnetic resonance spectroscopy (NMR). NMR is a well established tool for investigating the structure of molecules in the liquid state. It is increasingly being used to study molecular structures in the solid state. These studies have been hindered by the lack of a solid state standard from which to measure chemical shift data. Such a standard should be chemically inert, magnetically isotropic, and volatile. It should give a single sharp absorption line and it should absorb at a frequency higher than that of the samples to be measured. The new compound produced by the reaction of the subject invention has many of these properties and is a convenient standard for solid state NMR spectroscopy.

SUMMARY OF THE INVENTION

It is one object of the subject invention to provide a novel synthesis for $(CH_3)_3SiNSO$.

It is another object of the subject invention to provide a novel synthesis for $(CH_3)_3SiNSO$ which uses relatively inexpensive starting materials.

It is yet another object of the subject invention to provide a novel synthesis for $(CH_3)_3SiNSO$ which goes to 100% completion at ambient temperatures.

It is another object of the invention to provide a method for measuring the concentration of $SO_2$ in gases.

It is still another object of the invention to provide a method for measuring the concentration of $SO_2$ in gases which allows samples to be taken at remote sites far from the analytical laboratory.

It is still another object of the invention to provide a method for measuring the concentration of $SO_2$ in gases which is accurate and reliable at low levels of $SO_2$ concentration.

Finally, it is a further object of the invention to provide a new material which can be used as a standard in solid-state nuclear magnetic resonance spectroscopy and a method for making the new material.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

In accordance with the invention, $SO_2$ is reacted with the common liquid silylating agent $((CH_3)_3Si)_2NH$, hexamethyldisilazane (HMDS), under any of several possible sets of reaction conditions. The reaction goes to 100% completion at ambient temperatures. The products include liquid $(CH_3)_3SiNSO$ or 1,1,1-trimethyl-N-sulfinylsilanamine, solid $[NH_4][(CH_3)_3SiOSO_2]$ or ammonium trimethylsilylsulfite, and liquid $((CH_3)_3Si)_2O$ or hexamethyldisiloxane. The stoichiometry of the reaction has been determined to be:

$$4((CH_3)_3Si)_2NH + 4SO_2 \rightarrow 3(CH_3)_3SiNSO + [NH_4][(CH_3)_3SiOSO_2] + 2((CH_3)_3Si)_2O$$

The reaction provides a synthesis of $(CH_3)_3SiNSO$ which may be accomplished simply by mixing the two starting reagents.

The reaction of the subject invention may also be used in a method for determining the concentration of $SO_2$ in gases such as ambient air. The product $(CH_3)_3SiNSO$ fluoresceses at 450 nm and the product $[NH_4][(CH_3)_3SiOSO_2]$ fluoresces at 350 nm. By the method of the subject invention a known volume of air or other sample gas is pumped through a small vial of HMDS. This may be done at a remote site such as an urban area or in a primitive forest. The vial is capped and returned to the laboratory. The fluorescence of either product is then measured. The concentration of $SO_2$ is determined by comparing the measured fluorescence with predetermined calibration curves. For added accuracy, a laser light source may be used to excite the fluorescent reaction products to increase the sensitivity of the method at low levels of $SO_2$. Thus, the reaction of the subject invention can be used in a portable inexpensive method of $SO_2$ determination which is highly specific and sensitive at low $SO_2$ levels.

The new reaction product $[NH_4][(CH_3)_3SiOSO_2]$ is of further interest. Its trimethylsilyl group is similar to the common liquid NMR standard, tetramethylsilane. It is a volatile white solid with unusual properties which make it useful as a solid-state standard for nuclear magnetic resonance spectroscopy for both $^1H$ and $^{13}C$ work. Because of its high vapor pressure, it may readily be sublimed wherever it is needed. It may be sublimed onto a sample in an NMR tube on a vacuum line, the spectrum taken, than the salt may be sublimed off the sample and the spectrum of the pure sample recorded. As the trimethylsilyl group is the most widely used functional group standard, all results will be consistent with the current data in the literature.

BRIEF DESCRIPTION OF THE DRAWINGS

FIG. 1 is a typical calibration curve used in the determination of the concentration of $SO_2$ in gases. The fluorescence of $[NH_4][(CH_3)_3SiOSO_2]$ as measured in millivolts is plotted against the concentration of $SO_2$ as measured in $\mu g/l$ equivalent $SO_2$ based on a 200 liter sample.

FIG. 2 is an infrared spectrum of a solid film of $[NH_4][(CH_3)_3SiOSO_2]$.

DETAILED DESCRIPTION OF THE PREFERRED EMBODIMENT

The following is a detailed description of the preferred embodiment of the invention. Other embodiments will be readily apparent to those skilled in the art.

The subject invention involves the reaction of $SO_2$ with the common silylating agent $((CH_3)_3Si)_2NH$, hexamethyldisilazane (HMDS). The stoichiometry of the reaction is described above. The reaction may be carried out by simple mixing of the two reagents, such as by bubbling $SO_2$ through pure HMDS or dilute HMDS-pentane solution. Stringent conditions of reagent purity are not required as long as excess moisture is excluded. Preferably, the reaction is run under an inert atmosphere such as nitrogen or a modest vacuum at low temperatures, although this is not strictly necessary.

If very pure reaction products are desired, an alternative procedure may be employed. HMDS in a reaction vessel is cooled to liquid nitrogen temperatures and degassed on a high vacuum line. A measured amount of $SO_2$ is added to the vessel such that the ratio of HMDS to $SO_2$ ranges from 1:1 to 1:3. At these reduced temperatures, both reactants are solids. The vessel is sealed off and the mixture is allowed to warm to room temperature. Almost immediately upon melting, the reaction proceeds to completion, as indicated by the formation of the finely divided white solid, $[NH_4][(CH_3)_3SiOSO_2]$.

The reaction products may be separated in several different ways. The product mixture is removed from the vessel as a pentane slurry and filtered to separate the white solid $[NH_4][(CH_3)_3SiOSO_2]$. The pentane is removed from the filtrate by evaporation in a stream of dry nitrogen. The two liquid products, $(CH_3)_3SiNSO$ and $((CH_3)_3Si)_2O$, are then separated and purified by gas chromatography. Alternatively, the liquid may be separated from the solid by vacuum distillation, but because of the high volatility of the solid, the distillation must be performed at either reduced temperatures or with a multiple trap system. In either case, the liquid products adhere to the solid and the solid is slightly soluble in the liquid, so that total separation can be difficult. Once separated, the liquid product should be stored in a dry atmosphere because it reacts slowly with moisture in the air, leaving a solid white residue on the vessel walls.

EXAMPLE

A reaction vessel fitted with a Teflon ® stopcock was charged with 0.42 moles of HMDS. The vessel and its contents were brought to $-196°$ C. and the sample was degassed. 1.30 moles of $SO_2$ were condensed into the vessel, and the vessel was sealed off and allowed to warm to ambient temperature. As the mixture melted, a yellow solid appeared. The yellow color quickly disappeared, leaving a colorless liquid fraction and the fluffy white solid. The reaction appeared to be complete before the system reached 0° C. After the reaction was complete, the unreacted $SO_2$ was recovered and measured as an ideal gas. In this example, 0.85 moles of $SO_2$ were recovered.

This reaction may be used to analyze gases such as ambient air or industrial stack gases for $SO_2$ concentration. The new method uses the fact that two of the reaction products, $(CH_3)_3SiNSO$ and $[NH_4][(CH_3)_3SiOSO_2]$, fluoresce at different wavelengths. By the basic method of the invention, a sample of gas usually in the range of 10 to 200 liters is pumped via a portable pump through a vial containing approximately 2 to 5 ml of HMDS solution. This may be done at a remote site such as an urban area or in a primitive forest. The volumes of the gas sample and the HMDS may be varied with the type of gas being tested. For example, a larger volume of gas may be required for a gas with low $SO_2$ concentration, such as ambient air, while gases such as industrial stack gases with higher $SO_2$ concentration may require smaller gas sample volumes. When the gas sample is pumped through the HMDS solution, any $SO_2$ present in the sample will react as previously described. The vial is securely stoppered to exclude air and excess moisture and returned to the laboratory. The reacted liquid is transferred to a quartz fluorimetry cell and the fluorescence of either product is measured by standard fluorimetric techniques. The concentration of $SO_2$ in the gas sample is then determined by comparing the measured fluorescence to a predetermined calibration curve.

The fluorescense of either product may be measured. The liquid product $(CH_3)_3SiNSO$ is excited at about 240, 270, 300 and 350 nm and emits at about 450 nm. The solid may be excited at about 240, and 300 nm. In any non-quenching solvent, the solid will fluoresce at about 350 nm. It has been found that excitation at 300 nm provides particularly good sensitivity. The fact that the two fluorescent products offer several wavelengths of excitation and wavelengths of detection allows the analyst to choose wavelengths such that known interferences in the solution such as atmospheric hydrocarbons or oxides may be avoided. In addition, measurements of a single sample may be made at different wavelengths to provide a cross-check for accuracy and reliability.

FIG. 1 shows a typical calibration curve for use in this method of analysis. This particular curve is for the fluorescence of $[NH_4][(CH_3)_3SiOSO_2]$ dissolved in methanol at approximately 23° C. The wavelength of excitation from a laser source was 236 nm, and the wavelength of detection was 350 nm. The fluorescent intensity is measured in millivolts. The concentration of $SO_2$ is expressed in terms of $\mu g/l$ equivalent $SO_2$ based on a 200 liter gas sample. The optical equipment used such as the photomultiplier, optional monochrometer, and filter are the standard equipment typically used in the art. The excitation source was an $N_2$-pumped pulsed dyelaser doubled in frequency with a potassium pentaborate crystal. The starting energy was 0.7 Mw. The pulses were of a duration of 5 nsec at a frequency of 20 Hz. The total energy transmitted to the sample was 4 u joules per pulse. The fluorescence was measured at 90° from the incident light, as is standard procedure. Obviously, more accurate results could be obtained by optimizing the optical system according to procedures well known to those skilled in the art. For example, a laser of higher intensity could be used to give much greater sensitivity, especially at low $SO_2$ concentrations.

The HMDS through which the sample gas is bubbled may be present as any of several types of solution. The HMDS may be present as the neat solution. Alternatively, the HMDS may be dissolved in an aliphatic hydrocarbon solvent such as pentane. Such solvents are commonly used in fluorescence techniques because they are non-fluorescent and non-quenching. Heavier hydrocarbons such as octane or nonane could be used to reduce evaporation during the bubbling step. Cyclohexane has also been used but its high vapor pressure can result in large solvent losses due to evaporation. Finally, the HMDS can float on top of a dense and more polar solvent such as ethanol or methanol. This not only prevents solvent evaporation but the solid product $[NH_4][(CH_3)_3SiOSO_2]$ readily dissolves in the polar solvent as the reaction proceeds.

Thus, it is clear that the method of the subject invention provides a simple and inexpensive method of $SO_2$ analysis of gases which allows samples to be taken at remote sites. The method is sufficiently flexible in both the method of taking samples and the method of analysis to allow for a wide variety of gases to be analyzed.

The reaction of the subject invention produces a new solid compound believed to have the formula $[NH_4][(CH_3)_3SiOSO_2]$. It has an unusually high vapor pressure ranging from 0.5 torr at 4.6° C. to 19.0 torr at 49.0° C. It also has a very low bulk density. Its heat of sublimation is approximately 15 kcal $mole^{-1}$. The compound is unique in that it can be readily sublimed wherever it is needed without undergoing decomposition. It is very soluble in polar solvents such as dimethylsulfoxide and methanol and is virtually insoluble in non-polar solvents such as dichloromethane, benzene, toluene, cyclohexane, pentane, ether and acetonitrile. Infrared spectra of the solid taken by different techniques are listed in Table I.

TABLE I

Infrared Spectra of $NH_4(CH_3)_3SiOSO_2$ Absorptions ($cm^{-1}$)

| Solid Film | Nujol Mull | KBr Pellet |
|---|---|---|
| 3220 sh | | |
| 3190 vs | 3190 s | |
| 3065 vs | | |
| 2990 sh | Nujol ® | 3100 |
| 2910 s | | vvbr |
| 2100 vw | 2100 vw | |
| 1840 vw | 1840 vw | |
| 1475 sh | | |
| 1450 sh | | |
| 1425 m | Nujol ® | 1390 |
| 1385 sh | | vbr |
| 1355 w | | |
| 1283 sh | | |
| 1265 s | 1265 m | |
| 1160 m | 1170 m | 1165 m |
| 1075 s | 1080 sh | 1085 m |
| 1060 s | 1065 s | |
| 965 m | 965 m | 1065 m |
| 920 sh | 890 sh | 975 s |
| 865 s | 860 s | |
| 820 sh | 830 sh | |
| 775 m | 775 m | |
| | 737 w | |
| 708 vw | 670 s | 660 s |
| 672 m | 630 s | 625 m |
| 630 m | 538 w | 560 m |
| 540 m | 538 w | |
| | 510 m | |
| | 440 m | | sh = shoulder, vs = very strong, s = strong, m = medium, w = weak, vw = very weak, vbr = very broad, vvbr = very very broad.

The Nujol ® Mull and KBr pellet spectra were taken by standard techniques. A more unusual procedure was used for the solid film spectrum, shown in FIG. 2. A sample of the solid was introduced into a conventional gas IR cell which was then evacuated, leaving pure solid and vapor. One of the windows of the cell was cooled, whereupon a film of solid formed on the window via sublimation. The cell was allowed to warm to ambient temperature and the spectrum of the solid film was easily obtained.

For further identification of the new compound, a Raman spectrum was taken with an $Ar^+$ ion laser source. The data from the Raman spectrum are listed in Table II.

TABLE II

Raman Spectrum of $[NH_4][(CH_3)_3SiOSO_2]$ Absorptions ($cm^{-1}$)

| | | |
|---|---|---|
| 3040 vw | 902 vw | 535 m |
| 2962 m | 850 w | 443 m |
| 2906 s | 818 vw | 398 w |
| 1420 w | 768 vw | 322 w |
| 1277 vw | 698 w | 291 m |
| 1052 vs | 656 m | 247 vs |
| 949 vw | 624 s | 220 vw | vs = very strong, s = strong, m = medium, w = weak, vw = very weak.

This new compound has practical applications in the field of nuclear magnetic resonance (NMR) spectroscopy. The principles of NMR are described in *Applications of Absorption Spectroscopy of Organic Compounds*, John R. Dyer, 1965, Prentice-Hall, Inc., pp. 58–132. The new compound contains a trimethylsilyl group very similar to the common nuclear magnetic resonance liquid standard tetramethylsilane (TMS). The resonance of the methyl protons of the solid material in methanol solution is at $\delta = -0.10$ ppm referenced to TMS. The $^{13}C$ NMR chemical shift of the methyl carbon atoms in methanol solution is also upfield from TMS at $\delta^{13}C = -2.35$ ppm.

The presence of the trimethylsilyl group in a highly volatile solid permits the compound to be used as a standard in solid state NMR spectroscopy. Three techniques are commonly used to obtain high resolution NMR spectra of solid state materials. As described briefly by R. G. Griffin, *Anal. Chem.*, 1977, 49, 951A, these include magic angle sample spinning (MASS), multiple pulse techniques, and magnetic dilution. $[NH_4][(CH_3)_3SiOSO_2]$ may be used as a standard with all of these techniques, but it is particularly well suited to the MASS method. In this method, the sample is rotated very rapidly to narrow the spectral lines. If the axis of rotation is chosen as the "magic angle" 54°54′, the angle of the diagonal of a cube, the anisotropic broadening interactions are largely removed from the spectrum. The spectrum then exhibits the same kinds of fine structure as is found in the high resolution NMR spectra of fluids. In the application of the subject invention, the sample whose spectrum is to be taken may be oriented along the desired axis and $[NH_4][(CH_3)_3SiOSO_2]$ may be sublimed onto the sample. The spectrum may then be taken with the standard oriented along the same axis of rotation as the sample. If desired, the standard may then be sublimed off the sample and a spectrum of the pure sample recorded. The main advantages of the invention are the easy application and removal of the standard and the fact that its chemical shift is very similar to the common liquid standard tetramethylsilane. In addition, the new standard may be used with samples that are either bulk crystals or finely divided solids.

The foregoing description of a preferred embodiment is not intended to limit the invention to the precise form disclosed. Obviously, many modifications and variations are possible in light of the above teaching. The embodiment was chosen and described in order to best explain the principles of the invention and its practical application.

The embodiments of the invention in which an exclusive property or privilege is claimed are defined as follows:

1. A method of analyzing the $SO_2$ content in a sample of gas comprising:
   pumping a known volume of the gas through a known volume of $((CH_3)_3Si)_2NH$, to react any $SO_2$ in the gas with the $((CH_3)_3Si)_2NH$ to form the compounds $(CH_3)_3SiNSO$ and $[NH_4][(CH_3)_3SiOSO_2]$,
   exciting at least one of the compounds so formed to induce fluorescence; and
   measuring said induced fluorescence of at least one of said compounds whereby said measured fluorescence is determinative of the $SO_2$ content in the sample of gas.

2. The method of claim 1 wherein the $((CH_3)_3Si)_2NH$ is dissolved in an inert aliphatic hydrocarbon solvent selected from the group consisting of pentane, octane, nonane, and cyclohexane.

3. The method of claim 1 wherein the volume of the gas sample is between 10 and 200 liters.

4. The method of claim 3 wherein the volume of $((CH_3)_3Si)_2NH$ is between 2 and 5 milliliters.

5. The method of claim 1 wherein the $((CH_3)_3Si)_2NH$ is floated on top of a polar solvent whereby $[NH_4][(CH_3)_3SiOSO_2]$ dissolves in the polar solvent as it is produced.

6. The method of claim 5 wherein the polar solvent is selected from the group consisting of ethanol and methanol.

7. The method of claim 1 wherein the fluorescence of $(CH_3)_3SiNSO$ is measured.

8. The method of claim 7 wherein the $(CH_3)_3SiNSO$ is excited by light having a wavelength selected from the group consisting of about 240 nm, about 270 nm, about 300 nm, and about 350 nm.

9. The method of claim 8 wherein said induced fluorescence is measured at a wavelength of detection of about 450 nm.

10. The method of claim 1 wherein the fluorescence of $[NH_4][(CH_3)_3SiOSO_2]$ is measured.

11. The method of claim 10 wherein the $[NH_4][(CH_3)_3SiOSO_2]$ is excited by light having a wavelength selected from the group consisting of about 240 nm and about 300 nm.

12. The method of claim 11 wherein said induced fluorescence is measured at a wavelength of detection of about 350 nm.

* * * * *